(12) United States Patent
Al-Zaydi

(10) Patent No.: US 8,278,477 B2
(45) Date of Patent: Oct. 2, 2012

(54) METHOD FOR MAKING A PHOSPHORUS YLIDE

(75) Inventor: Khadijah M. Al-Zaydi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 406 days.

(21) Appl. No.: 12/654,499

(22) Filed: Dec. 22, 2009

(65) Prior Publication Data

US 2011/0152565 A1 Jun. 23, 2011

(51) Int. Cl.
*C07C 69/74* (2006.01)
*C07C 229/48* (2006.01)

(52) U.S. Cl. ........................................ 560/122; 560/125
(58) Field of Classification Search .................. None
See application file for complete search history.

(56) References Cited

OTHER PUBLICATIONS

Al-Shiekh et al, ARKIVOC, Studies with 2-Arylhydrazono-3-oxopropanals: Routes for the Synthesis of Pyridazine-3,4-dicarboxylate and 3,5-Diaroylpyrazoles, 2008, 17, pp. 36-47.*

Al-Zaydi et al., "Microwave Assisted Condensation Reactions of 2-Aryl Hydrazonopropanals with Nucleophilic Reagents and Dimethyl Acetylenedicarboxylate," Molecules 12: 2061-2079 (2007).

* cited by examiner

*Primary Examiner* — Paul A Zucker
(74) *Attorney, Agent, or Firm* — Richard C. Litman

(57) ABSTRACT

The method for making a phosphorus ylide produces the ylide 2,3-bismethoxycarbonyl-4-phenyl-5-arylhydrazono-cyclopenta-1,3-dienyl-triphenylphosphonium in pure form by simple recrystallization of the reaction product. 3-Oxo-3-phenyl-2-(arylhydrozono)propanal and dimethylacetylenedicarboxylate are mixed in dichloromethane at room temperature. After cyclization of the intermediate (preferably at least two hours), triphenylphosphine is added to the mixture, ultimately resulting in formation of 2,3-bismethoxycarbonyl-4-phenyl-5-arylhydrazono-cyclopenta-1,3-dienyl-triphenylphosphonium. The product is recrystallized to produce 2,3-bismethoxycarbonyl-4-phenyl-5-arylhydrazono-cyclopenta-1,3-dienyl-triphenylphosphonium in pure form and in high yield. The aryl group may be any aromatic or aliphatic group.

5 Claims, 3 Drawing Sheets

Scheme 1

Scheme 2

Scheme 3

METHOD FOR MAKING A PHOSPHORUS YLIDE

BACKGROUND OF THE INVENTION

1. Field of the Invention

The present invention relates to phosphorus ylides and organic reaction schemes, and particularly to a method for making a phosphorous ylide, more particularly, 2,3-bis-methoxycarbonyl-4-phenyl-5-arylhydrazono-cyclopenta-1,3-dienyltriphenylphosphonium.

2. Description of the Related Art

Phosphorus ylides are reactive compounds that take part in many valuable reactions of organic synthesis, e.g., the conversion of aldehydes and ketones into alkenes through a Wittig reaction. The development of simple synthetic routes for widely used organic compounds from readily available reagents is one of the major tasks in organic chemistry. Phosphorous ylides are most often prepared by the treatment of a phosphonium salt with a base. Most of the phosphonium salts are usually made from the phosphine and an alkyl halide, and they are also obtained by the Michael addition of phosphorus nucleophiles to activated olefins.

One such phosphorus ylide is 2,3-bismethoxycarbonyl-4-phenyl-5-arylhydrazono-cyclopenta-1,3-dienyl-triphenylphosphonium. The synthesis of 2,3-bismethoxycarbonyl-4-phenyl-5-arylhydrazono-cyclopenta-1,3-dienyl-triphenylphosphonium has been previously reported, but in impure form as one product of a mixture of products. Separation of the ylide from the mixture is very difficult. So there is a necessity to synthesize this compound in pure form, preferably using an easy way.

It has been previously reported that the addition of triphenylphosphine to dimethyl acetylenedicarboxylate 2 in dichloromethane by stirring at room temperature produced the intermediate A, which was followed by the addition of arylhydrazonals 1, leading to the direct formation of dihydro-pyridiazine-5,6-dicarbonates 3 (see Scheme 1, shown in FIG. 1).

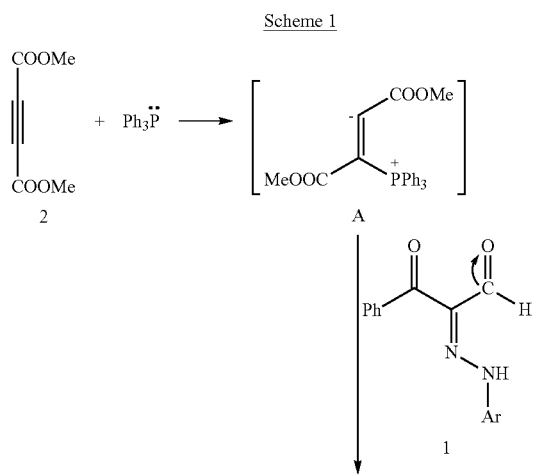

Scheme 1

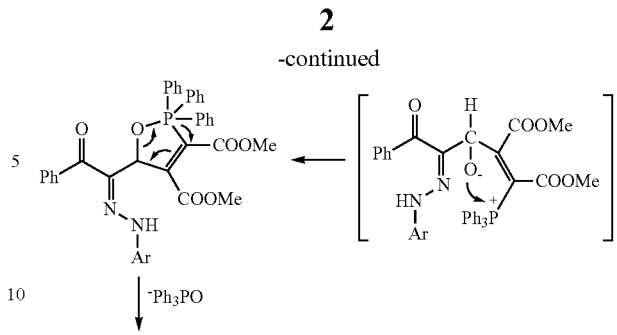

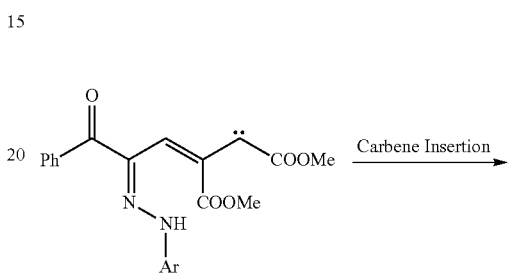

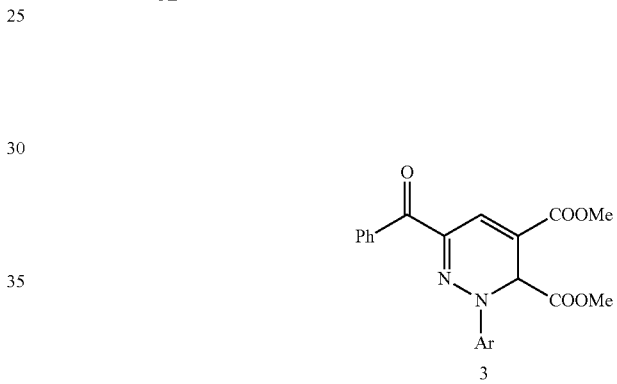

Ar = C₆H₄CN-o

On the other hand, when the addition of compound 1 to 2 is made under the normal conditions by stirring with dichloromethane at room temperature for some time, followed by addition of triphenylphosphine and continued stirring, the reaction furnished a mixture of two compounds (as examined by thin layer chromatography [TLC]). After separation and identification by elemental analysis and spectral data, it was found that one product was identified as compound 3 (40% yield), and other product was identified as compound 4 (60% yield) (see Scheme 2, shown in FIG. 2).

Scheme 2

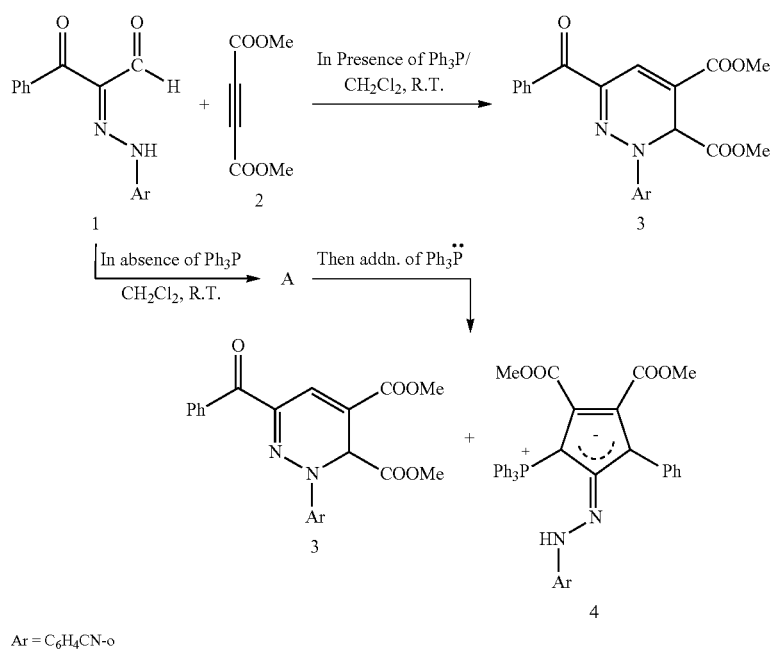

Ar = C$_6$H$_4$CN-o

Separation of compound 4 (2,3-bismethoxycarbonyl-4-phenyl-5-arylhydrazono-cyclopenta-1,3-dienyl-triphenylphosphonium) from the mixture of compounds 3 and 4 proves to be very difficult, and the yield is poor.

The compound 2,3-bismethoxycarbonyl-4-phenyl-5-arylhydrazono-cyclopenta-1,3-dienyl-triphenylphosphonium is an intermediate in the production of cyclopentene derivatives, as in the following reaction scheme.

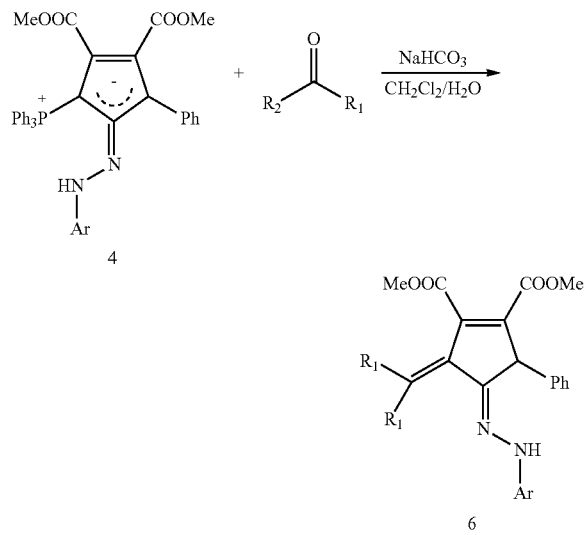

Cyclopentene derivatives are currently a matter of interest, since many have been found to have utility in inhibiting and treating tumors. See, e.g., U.S. Pat. No. 7,179,937, issued Feb. 20, 2007 to Gurjar et al. titled "Cyclopentanone Derivatives for Cancer Therapy."

It is desirable to provide a synthesis scheme that produces the ylide in high yield in pure form. Thus, a method for making a phosphorus ylide solving the aforementioned problems is desired.

SUMMARY OF THE INVENTION

The method for making a phosphorus ylide produces the ylide 2,3-bismethoxycarbonyl-4-phenyl-5-arylhydrazono-cyclopenta-1,3-dienyl-triphenylphosphonium in pure form by simple recrystallization of the reaction product. 3-Oxo-3-phenyl-2-(arylhydrozono)propanal and dimethyl acetylenedicarboxylate are mixed in dichloromethane at room temperature. After cyclization of the intermediate (preferably at least two hours), triphenylphosphine is added to the mixture, ultimately resulting in formation of 2,3-bismethoxycarbonyl-4-phenyl-5-arylhydrazono-cyclopenta-1,3-dienyl-triphenylphosphonium. The product is recrystallized to produce 2,3-bismethoxycarbonyl-4-phenyl-5-arylhydrazono-cyclopenta-1,3-dienyl-triphenylphosphonium in pure form and in high yield. The aryl group may be any aromatic or aliphatic group.

These and other features of the present invention will become readily apparent upon further review of the following specification.

DETAILED DESCRIPTION OF THE PREFERRED EMBODIMENTS

The method for making a phosphorus ylide produces the ylide 2,3-bismethoxycarbonyl-4-phenyl-5-arylhydrazono-cyclopenta-1,3-dienyl-triphenylphosphonium in pure form by simple recrystallization of the reaction product. 3-Oxo-3-phenyl-2-(arylhydrozono)propanal and dimethyl acetylenedicarboxylate are mixed in dichloromethane at room temperature. After cyclization of the intermediate (preferably at least two hours), triphenylphosphine is added to the mixture, ultimately resulting in formation of 2,3-bismethoxycarbonyl-4-phenyl-5-arylhydrazono-cyclopenta-1,3-dienyl-triphenylphosphonium. The product is recrystallized to produce 2,3-bismethoxycarbonyl-4-phenyl-5-arylhydrazono-cyclopenta-1,3-dienyl-triphenylphosphonium in pure form and in high yield. The aryl group may be any aromatic or aliphatic group. The synthesis of 2,3-bismethoxycarbonyl-4-phenyl-5-arylhydrazono-cyclopenta-1,3-dienyl-triphenylphosphonium is illustrated by the following example.

EXAMPLE

Figure 1:
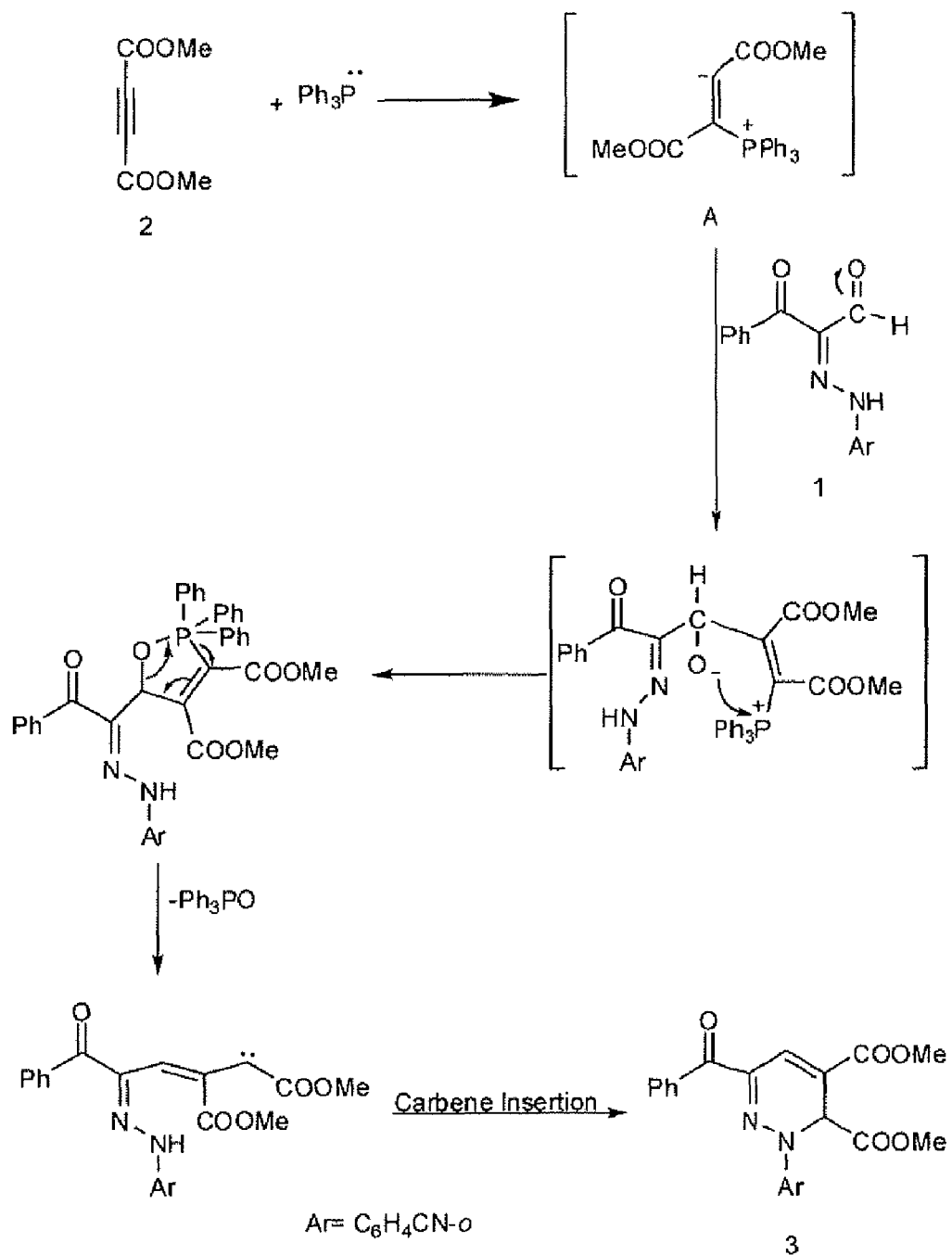
FIG. 1 is a chart showing a sequence of reactions (Scheme 1) for synthesizing dihydropyridiazine-5,6-dicarbonates according to the prior art.
Figure 2:
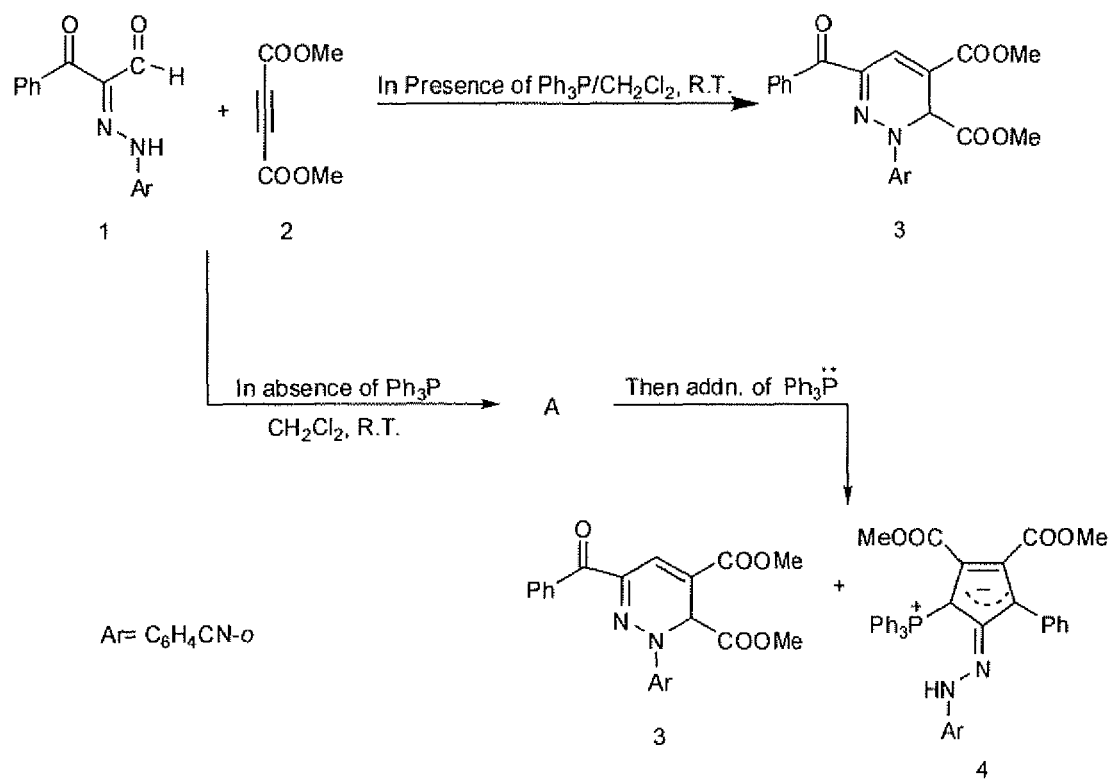
FIG. 2 is a chart showing a sequence of reactions (Scheme 2) for synthesizing 2,3-bismethoxycarbonyl-4-phenyl-5-arylhydrazono-cyclopenta-1,3-dienyl-triphenylphosphonium according to the prior art.
Figure 3:
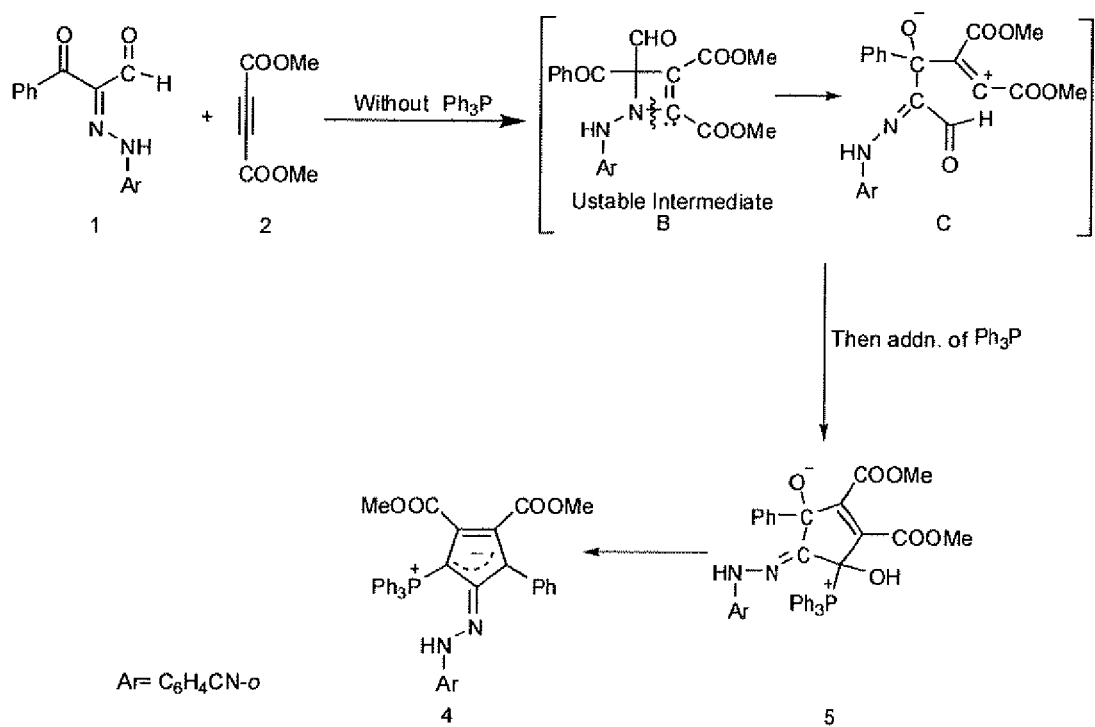
FIG. 3 is a chart showing a sequence of reactions (Scheme 3) for synthesizing 2,3-bismethoxycarbonyl-4-phenyl-5- arylhydrazono-cyclopenta-1,3-dienyl-triphenylphosphonium according to the present invention.

The reaction scheme is shown as Scheme 3, shown in FIG. 3. All melting points were measured on Gallenkamp electrothermal melting point apparatus and are uncorrected. IR absorption spectra were measured on a Nicolet Magna 520FT IR spectrophotometer. $^1$H NMR and $^{13}$C NMR spectra were recorded in deuterated dimethlsulfxide (DMSO-d6) on a Bruker DPX400 MHz spectrometer using tetramethylsilane (TMS) as an internal reference. Mass spectra were performed on a Shimadzu GCMS-QP1000 Ex mass spectrometer at 70 eV. Elemental analyses were measured by means of a Perkin Elmer 2400 CHN Elemental analyzer flowchart. X-ray crystallography was carried out on a Kappa CCD Enraf Nonius FR 590 diffractometer, National Research Center, Dokki, Cairo, Egypt.

An equimolar mixture of compounds 1 and 2 (0.01 mole) in $CH_2CL_2$ was stirred at room temperature (28-30° C.) for 2 hours, then triphenylphosphine (0.01 mole) was added with continued stirring at room temperature overnight (about 14 hours). Then the solvent was evaporated under reduced pressure, and the product was recrystallized from ethanol to give compound 4 in 91% yield; orange crystals; m.p. 175° C.; IR: $v_{max}$ cm$^{-1}$: 3416 (NH), 2229 (CN) and 1746 (C=O ester); $^1$H NMR (400 MHz DMSO-d6): δ=2.75 (d, 1H, $J_{HP}$=14.4, cyclopentane H, 3.70 (s, 3H, $OCH_3$), 3.77 (s, 3H, $OCH_3$), 6.16-7.92 (m, 24H, Ar—H), 11.22 (s, 1H, NH, $D_2O$ exchangeable) ppm; $^{13}$C-NMR (100 MHz DMSO-d6): δ=45.28, 48.99, 50.55, 50.81, 100.32, 111.45, 113.00, 117.58, 117.62, 121.59, 123.55, 124.29, 126.85, 128.49, 128.63, 132.81, 133.52, 136.48, 142.20, 147.82, 150.45, 116.50 (CN), 165.05, 171.20 (2$COOCH_3$); MS: 650 (M$^+$); Anal. Calcd. For $C_{40}H_{33}N_3O_4P$ (650.68): C, 73.83; H, 5.11; N, 6.46 Found: C, 73.92; H, 5.08; N, 6.40%.

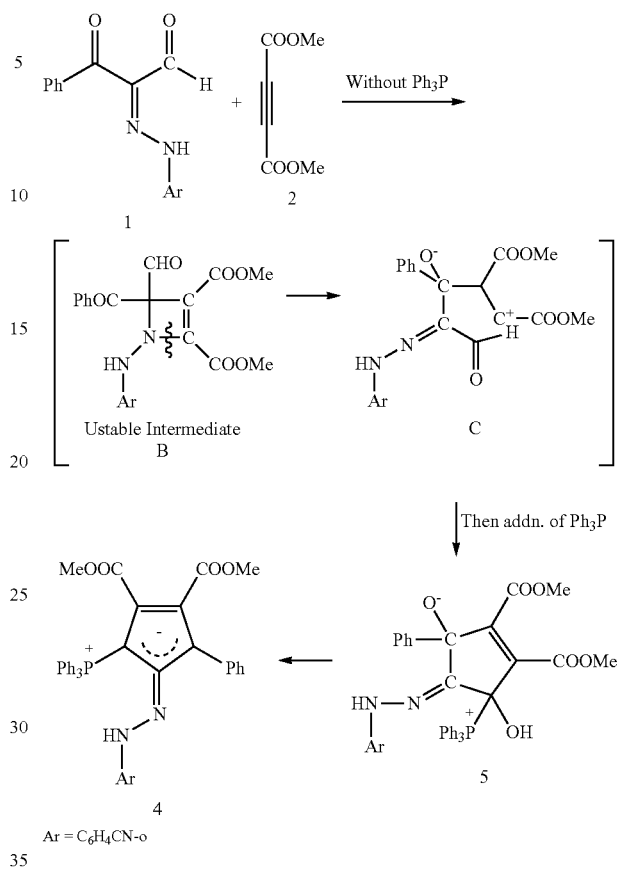

Scheme 3

Ar = $C_6H_4CN$-o

The structure of the compound 4 was further unequivocally confirmed by X-ray crystallography. Single crystal X-ray diffraction of compound 4 adds sharp evidence for the proposed structure. The formation of compound 4 was assumed to occur by cycloaddition of compounds 1 and 2, which gives the unstable four-membered ring B, which then undergoes rearrangement to the intermediate C. This is followed by addition of triphenylphosphine, resulting in nucleophilic attack to the aldehyde group, and finally deoxygenation of compound 5 to yield the new polyfunctional phosphonium cyclopentenyl salt 4.

It is to be understood that the present invention is not limited to the embodiments described above, but encompasses any and all embodiments within the scope of the following claims.

I claim:
1. A method for making 2,3-bismethoxycarbonyl-4-phenyl-5-arylhydrazono-cyclopenta-1,3-dienyltriphenylphosphonium, comprising the steps of:
   adding 3-oxo-3-phenyl-2-(arylhydrozono)propanal to dimethyl acetylenedicarboxylate in dichloromethane at room temperature to form an intermediate;
   after cyclization of the intermediate, adding triphenylphosphine to the mixture to form crude 2,3-bismethoxycarbonyl-4-phenyl-5-arylhydrazono-cyclopenta-1,3-dienyltriphenylphosphonium; and
   recrystallizing the crude 2,3-bismethoxycarbonyl-4-phenyl-5-arylhydrazono-cyclopenta-1,3-dienyltripbenylphosphonium to recover pure product.

2. The method for making 2,3-bismethoxycarbonyl-4-phenyl-5-arylhydrazono-cyclopenta-1,3-dienyltriphenylphosphonium according to claim 1, wherein the aryl group in the 3-oxo-3-phenyl-2-(arylhydrozono)propanal comprises an aromatic or an aliphatic substituent.

3. The method for making 2,3-bismethoxycarbonyl-4-phenyl-5-arylhydrazono-cyclopenta-1,3-dienyltriphenylphosphonium according to claim 1, wherein said step of adding triphenylphosphine to the mixture is performed at least two hours after said step of adding 3-oxo-3-phenyl-2-(arylhydrozono)propanal to dimethyl acetylenedicarboxylate.

4. The method for making 2,3-bismethoxycarbonyl-4-phenyl-5-arylhydrazono-cyclopenta-1,3-dienyltriphenylphosphonium according to claim 1, further comprising the step of allowing the mixture to stand overnight at room temperature with continuous stirring after said step of adding triphenylphosphine to the mixture and before said step of recrystallizing the crude 2,3-bismethoxycarbonyl-4-phenyl-5-arylhydrazono-cyclopenta-1,3-dienyltriphenylphosphonium.

5. A method for making 2,3-bismetboxycarbonyl-4-phenyl-5-arylhydrazono-cyclopenta-1,3-diertyltriphenylphosphonium, comprising the steps of:
  adding 3-oxo-3-phenyl-2-(arylhydrozono)propanal to dimethyl acetylenedicarboxylate in dichloromethane at room temperature to form an intermediate;
  allowing the mixture to stand at room temperature with continuous stirring for at least two hours;
  adding triphenylphosphine to the mixture to form crude 2,3-bismethoxycarbonyl-4-phenyl-5-arylhydrazono-cyclopenta-1,3-dienyltriphenylphosphonium; and
  recrystallizing the crude 2,3-bismethoxycarbonyl-4-phenyl-5-arylhydrazono-cyclopenta-1,3-dienyltriphenylphosphonium to recover pure product.

* * * * *